(12) United States Patent
Hocker et al.

(10) Patent No.: US 9,366,579 B2
(45) Date of Patent: Jun. 14, 2016

(54) THERMAL PROCESS CONTROL

(71) Applicant: John Bean Technologies Corporation, Chicago, IL (US)

(72) Inventors: Jon A. Hocker, Bothell, WA (US); John R. Strong, Bellevue, WA (US); Ramesh M. Gunawardena, Chagrin Falls, OH (US)

(73) Assignee: John Bean Technologies Corporation, Chicago, IL (US)

( * ) Notice: Subject to any disclaimer, the term of this patent is extended or adjusted under 35 U.S.C. 154(b) by 48 days.

(21) Appl. No.: 14/139,541

(22) Filed: Dec. 23, 2013

(65) Prior Publication Data

US 2014/0220197 A1     Aug. 7, 2014

Related U.S. Application Data

(60) Provisional application No. 61/745,414, filed on Dec. 21, 2012.

(51) Int. Cl.
| | |
|---|---|
| *G01K 13/06* | (2006.01) |
| *G01K 13/00* | (2006.01) |
| *A22C 17/00* | (2006.01) |
| *G01N 33/12* | (2006.01) |
| *A23L 3/18* | (2006.01) |
| *G01K 13/12* | (2006.01) |
| *G01N 33/02* | (2006.01) |
| *B65G 47/53* | (2006.01) |

(52) U.S. Cl.
CPC .............. *G01K 13/00* (2013.01); *A22C 17/008* (2013.01); *A23L 3/185* (2013.01); *G01K 13/06* (2013.01); *G01K 13/12* (2013.01); *G01N 33/02* (2013.01); *G01N 33/12* (2013.01); *B65G 47/53* (2013.01); *G01K 2207/06* (2013.01)

(58) Field of Classification Search
CPC ........ G01N 33/02–33/12; G01K 13/04–13/08; G01K 13/12; G01K 2207/00–2207/08; G01K 13/00; A22C 17/0073–17/008; A23L 3/185; B65G 47/53
USPC ............. 426/231–233; 374/149, 155; 99/328, 99/329 R, 333, 337, 338
See application file for complete search history.

(56) References Cited

U.S. PATENT DOCUMENTS

| | | | | |
|---|---|---|---|---|
| 4,990,347 A | * | 2/1991 | Rasmussen | A23L 3/003 426/231 |
| 5,082,373 A | * | 1/1992 | Rohde | A22B 5/0064 374/155 |
| 5,179,265 A | * | 1/1993 | Sheridan | A21B 1/245 219/388 |
| 5,253,564 A | * | 10/1993 | Rosenbrock | A21B 1/40 99/326 |
| 5,585,603 A | * | 12/1996 | Vogeley, Jr. | G01G 9/005 177/1 |
| 5,668,634 A | * | 9/1997 | Newman | G01N 33/12 348/89 |
| 5,876,771 A | * | 3/1999 | Sizer | A23L 3/225 426/231 |

(Continued)

*Primary Examiner* — Drew Becker
(74) *Attorney, Agent, or Firm* — Christensen O'Connor Johnson Kindness PLLC

(57) ABSTRACT

A thermal processing and control system (10) includes a thermal processing station (12) for receiving food products (14) being carried on a conveyor system (16). A first scanning station (18) is located upstream from a similar processing station (12) for scanning the food products being carried by the conveyor (16). A second scanning station (20) is located downstream of the thermal processing station (12). A diverter conveyor (24) diverts selected food products (14) from the conveyor (16) to a transverse conveyor (26) which is capable of positioning the diverted food product onto a temperature measurement station (28), whereat the temperature of the food product is measured, either manually or automatically.

34 Claims, 8 Drawing Sheets

(56) References Cited

U.S. PATENT DOCUMENTS

| | | | | | |
|---|---|---|---|---|---|
| 5,932,813 | A * | 8/1999 | Swartzel | | G01K 3/04 374/E3.004 |
| 6,062,728 | A * | 5/2000 | Breunsbach | | G01K 3/04 340/870.17 |
| 6,449,334 | B1 * | 9/2002 | Mazess | | G01N 23/06 378/53 |
| 6,826,989 | B1 * | 12/2004 | Wattles | | A22C 17/0093 83/102 |
| 6,866,417 | B2 | 3/2005 | Gunawardena | | G05D 23/1935 374/121 |
| 7,007,807 | B1 * | 3/2006 | Stockard | | A21B 1/48 209/592 |
| 7,038,172 | B1 * | 5/2006 | Stuck | | A47J 37/044 219/388 |
| 7,251,537 | B1 * | 7/2007 | Blaine | | A22C 17/0086 452/156 |
| 7,712,662 | B2 * | 5/2010 | Rock | | H04Q 9/00 235/375 |
| 9,016,458 | B2 * | 4/2015 | Bogle | | B65G 15/42 198/341.07 |
| 2001/0041150 | A1 * | 11/2001 | Weng | | A23L 3/027 422/3 |
| 2002/0004366 | A1 * | 1/2002 | Thorvaldsson | | A22C 17/0093 452/198 |
| 2002/0044590 | A1 * | 4/2002 | Simunovic | | G01K 1/022 374/176 |
| 2002/0054940 | A1 * | 5/2002 | Grose | | A22B 7/007 426/231 |
| 2005/0287252 | A1 * | 12/2005 | Schrock | | G01N 33/12 426/231 |
| 2007/0207242 | A1 * | 9/2007 | Carlsen | | A22B 5/007 426/231 |
| 2008/0103723 | A1 * | 5/2008 | Burdett | | G01K 1/02 702/130 |
| 2010/0008396 | A1 * | 1/2010 | Gaskins | | G01J 5/0022 374/141 |
| 2010/0179684 | A1 * | 7/2010 | Blaine | | B07C 5/342 700/223 |
| 2012/0274470 | A1 * | 11/2012 | Sandvick | | G01N 33/02 340/584 |
| 2013/0128919 | A1 * | 5/2013 | Austen | | G01K 1/026 374/110 |
| 2013/0146672 | A1 * | 6/2013 | DePaso | | B65G 43/00 236/91 D |
| 2013/0302483 | A1 | 11/2013 | Riefenstein | | |
| 2014/0146849 | A1 * | 5/2014 | Randall | | G01K 1/14 374/141 |
| 2014/0369383 | A1 * | 12/2014 | Yousef | | G01K 3/14 374/137 |

* cited by examiner

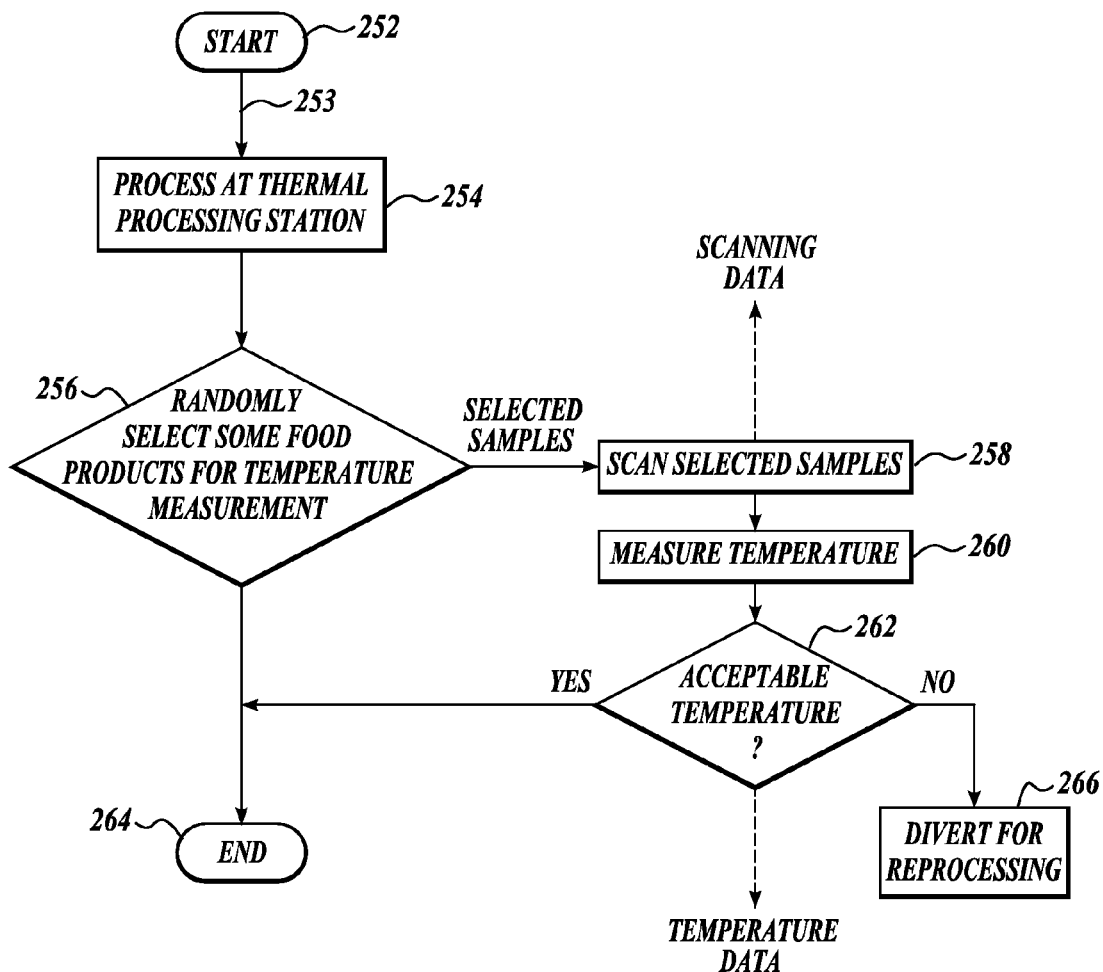

THERMAL PROCESS CONTROL

CROSS-REFERENCE TO RELATED APPLICATION

This application claims the benefit of U.S. Provisional Application No. 61/745,414, filed on Dec. 21, 2012, which is herein expressly incorporated by reference.

TECHNICAL FIELD

The present invention pertains to the thermal processing of work products, including particularly food products, and more specifically to measuring the temperature of thermally processed food products to determine the degree of thermal treatment applied to the food product, and making necessary adjustments to the thermal processing based on the results of the temperature measurements.

BACKGROUND

For obvious reasons, it is vitally important in the industrial food processing industry to fully cook food products prior to packaging. Such food products may not be subjected to any further step or process for killing bacteria prior to consumption of the food. Moreover, the performance of an industrial food processing system, such as an oven, fryer, steamer, roaster, chiller, or freezer can be significantly impacted by physical attributes of the food product, such as the thickness of the food product. Often, food product thickness can vary between batches or can trend thicker throughout a production shift without detection by personnel. If, for example, a new batch of food product enters a cooking process, and the average thickness of the new food product is larger than the thickness of the prior batch, it is desirable to proactively control the thermal process to insure proper cooking. Such proactive control is not widely practiced today. Typically, the control process is largely reactive. When an undercooked or otherwise underprocessed food product is detected as it leaves a thermal processing station, personnel typically respond by manually adjusting process settings.

The temperature of the food product leaving the thermal processing station is typically measured manually by inserting a thermal couple probe into the processed food product hopefully at or near the mass center of the workpiece. However, it is difficult for personnel to accurately determine where the mass center of the workpiece is located. An additional difficulty and source of temperature measurement error exists in placing the temperature probe at the estimated center of the workpiece even if the operator believes that he or she has identified the mass center. Moreover, a further source of error occurs when the measuring tip of the probe is positioned in what is thought to be the mass center of the workpiece, but in actuality is a void in the workpiece. A slight change in the position of a thermal probe can result in a significant difference in the temperature reading achieved, especially if the temperature probe is placed into a void in the workpiece.

Moreover, typically, the number of workpiece samples that are actually selected for temperature measurement is relatively small in relation to the number of workpieces being processed. Such relatively small sample size can be a source of temperature measurement error.

In an effort to reduce the likelihood of food products not being fully cooked or otherwise not sufficiently thermally processed, the current food industry practice is to adjust the cooking or other thermal process so that the center of the thickest workpieces reaches a desired temperature. However, this approach can result in a significant proportion of the workpieces being overly-cooked or otherwise overly-processed, which causes a decrease in yield as well as a decrease in profit because the overcooking or overthermal processing drives off moisture from the food product, resulting in reduction in the weight of the processed food product as well as its quality. Applicants estimate that eliminating the overcooking in a single process line can result in an economic savings of hundreds of thousands of dollars per year. This economic benefit arises from not having to cook or otherwise thermally process based on the thickest, largest, or otherwise maximum or extreme food product in the population being processed. Other benefits include (1) a reduction in labor required to monitor, control and report on the process, (2) a reduction in unscheduled sanitation procedures of the thermal processing system, including the thermal processing station and the conveyance systems removing the food product to and from the thermal processing station, as well as (3) increased production line operational time.

Because improperly or underthermally processed food products present a high safety risk, a highly hygienic solution is desired to ensure that the food products are fully cooked or otherwise fully thermally processed. As such, it is desirable to have minimal equipment situated over the food product traveling to a thermal processing station, during thermal processing at the thermal processing station, as well as traveling away from the thermal processing station, unless the equipment in question operates at a cooking temperature, or is otherwise maintained at a highly hygienic state. Complex equipment located over food product being thermally processed presents a contamination hazard since contaminated droplets of water or other moisture can fall on the cooked or otherwise processed food product.

In an effort to at least partially automate the temperature measurement function of cooked or otherwise processed food products, "pick-and-place" two-axis robots have been contemplated. The envisioned systems and equipment are situated over the food product stream, are used to remove selected food products from the food product stream and then transmit the food products to a temperature measurement location or station, where manual temperature measurement of the selected food product takes place. Concerns about this solution have prevented pick-and-place systems from being reduced to practice for thermal processes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure provides a method for measuring the internal temperature of discrete, thermally treated workpieces, which include the steps of selecting workpieces for temperature measurement from an output stream of workpieces exiting from a thermal processing system. Such selected workpieces are removed from the main stream of workpieces leaving the thermal processing system. Such selected workpieces are dimensionally characterized, for example, by scanning. Such characterization enables a determination to be made as to where on the selected workpiece the temperature measurement should take place. Such measurement can occur at one or more locations on the workpiece. The temperature measurement data can then be analyzed to determine the degree of thermal treatment that occurred in the workpiece. This information can be used to adjust the control parameters used in the thermal processing system.

In accordance with another aspect of the present method, the selected workpieces are removed to a temperature measurement station at which station the temperatures of the selected workpieces are measured. Such measurement can occur by using one or more probes inserted into the workpieces. Further, at selected intervals, the probes can be sanitized, so as to reduce the possibility of cross-contamination between different workpieces.

In a further aspect of the present method, the workpieces are carried away from the thermal processing system by a conveyor system. The selected workpieces can be removed from the conveyor system and transported to a temperature measurement station by a transport method that may include one or more conveyors, the use of gravity, the use of a gap or opening in the conveyor system, or by pressurized air jets that blow the workpieces off the conveyor system.

In another aspect of the method of the present disclosure, workpieces may be selected for temperature measurement from the output stream exiting the thermal processing system by random selection, by selecting the workpieces based on one or more physical attributes, such as size or thickness, or by sweeping across the workpiece stream and selecting workpieces from such sweeping procedure.

As a further aspect of the present invention, a method for controlling a thermal processing system for food products in a thermal processing station is provided. The method includes monitoring the stream of food products entering the thermal processing station to determine the physical attributes of all of the products passing into the thermal processing station, for example with an upstream scanner, and recording this data for use by a control subsystem of the thermal processing system. The process parameters of the thermal processing system are monitored, and the temperatures of selected food products exiting the thermal processing station are measured.

The method also includes modeling the thermal processing system by considering one or more of the following dynamics: (i) the manner in which changes in flow rate of the food products entering the thermal processing station results in changes to the temperature of the heat transfer fluid used to thermally process the food products; (ii) the manner in which changes in the geometry or condition of the food products entering the food processing station causes changes to the rate of temperature change in the food products in the thermal processing station; and (iii) changes in the temperature of the food products exiting the thermal processing station relative to the changes in the operating conditions of the thermal processing system or changes in the flow rate or physical attributes of the food products entering the food processing station. If the modeling results indicate that the measured temperatures of the food products exiting the thermal processing station are beyond a desired temperature range, that control system adjusts the thermal processing system process parameters, or recommends adjustments be made to the processing parameters of the thermal processing system.

In addition to selecting such food products based on one or more physical attributes, by random selection or by sweeping across the stream of food products, if the upstream scanner detects a changed population of workpieces (e.g., suddenly thicker or thinner, etc.) or if thermal processing control parameters have changed, for example, based on the modeling results, then after one residence time in the thermal processing system, it is desirable to measure the temperature of the exiting food products to determine if the changes are causing a problem and/or if the automatic or recommended adjustments to the operation of the thermal processing system resolved the problem in time.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 8 is a flow diagram of a second method of the present disclosure.

DETAILED DESCRIPTION

In the Detailed Description, the reference to "food product" is to be understood to also refer to "food piece," "work product" or "workpiece."

Figure 1:
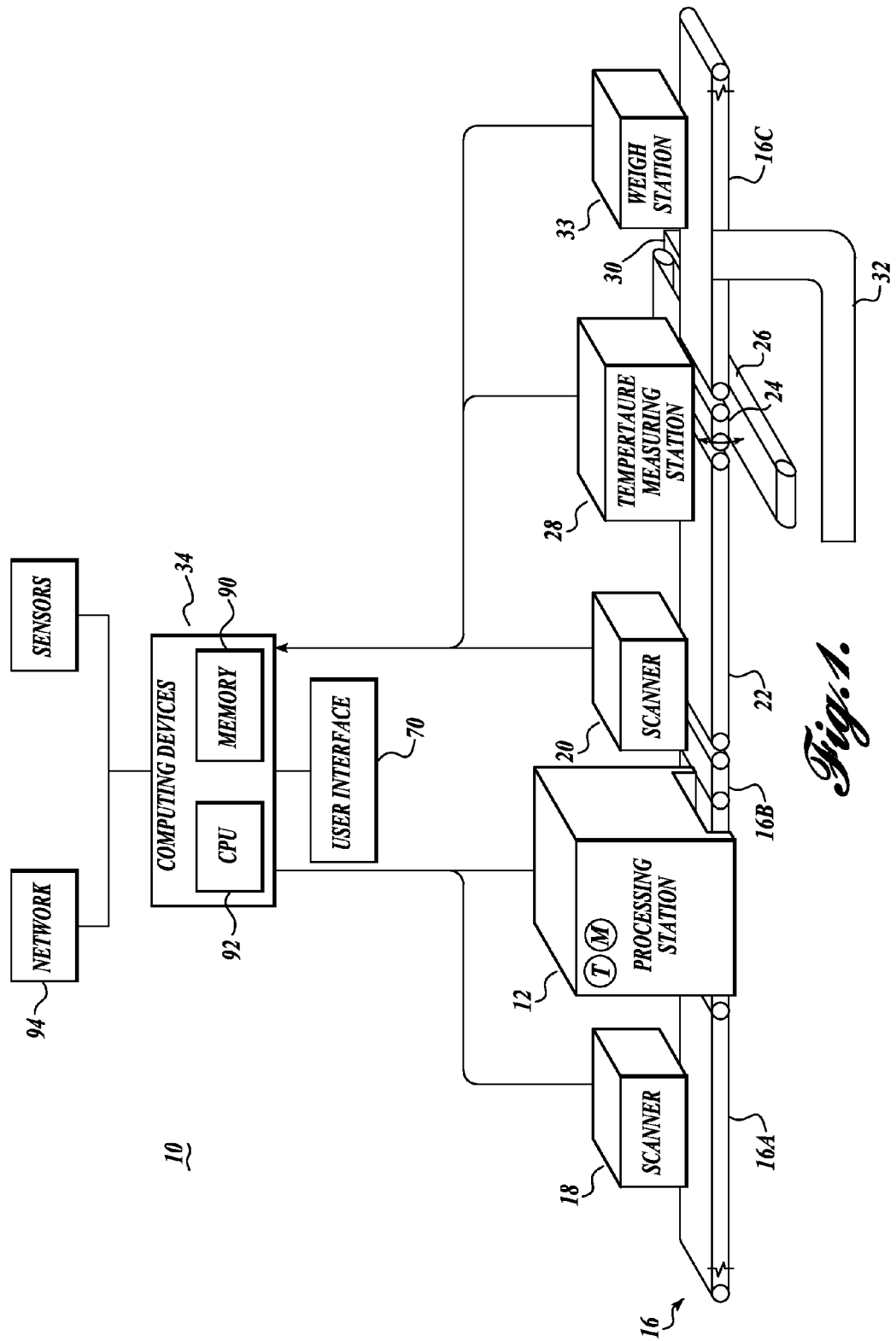
FIG. 1 is a schematic view of a thermal process control system of the present disclosure.

Referring initially to FIG. 1, a thermal processing and control system 10 in accordance with the present disclosure includes a thermal processing station 12 for receiving work products, for example, in the form of food products 14 via the infeed section 16A of a conveyor system 16. The conveyor system 16 may itself travel through the thermal processing station 12, or the thermal processing station may have its own conveyor system(s). Upstream from thermal processing station 12, conveyor section 16A carries food products 14 past a first scanning station 18 for scanning the food products 14 being carried by the conveyor section 16A.

A second section 16B of conveyor 16 carries away food products 14 that have been processed at station 12. In this regard, food products are carried to a second scanning station 20 having its own conveyor section 22 positioned in registry with conveyor section 16B. See also FIGS. 2 and 3. The conveyor section 22 is also in registry with a diverter conveyor section 24 capable of diverting food products 14 to an underlying transverse conveyor 26. The transverse conveyor 26 is capable of positioning diverted food products at a temperature measurement station 28, whereat the temperature of the food product can be measured either manually or automatically. The transverse conveyor 26 is in registry with a receptacle 30 at the opposite end of the transverse conveyor from the location of the temperature measurement station 28. At the temperature measurement station, the transverse conveyor may be in registry with a return conveyor 32, that is capable of transporting the food product, after the temperature of the food product has been measured, back to the flow stream of conveyor 16, or to another desired location. An optional weighing station 33 is located downstream of this rejoinder location to weigh the food products 14 that proceed to the next processing station.

The system 10 also includes a computing device 34 that may be incorporated into either scanning station 18 or 20 or may be independent of such scanning station(s). The computing device is capable of receiving the scanning information from scanning stations 18 and 20, the temperature information from temperature measurement station 28, as well as receiving and sending information pertaining to the operation and control of a thermal processing station 12. As explained below, the information from the scanners as well as the temperature measurement station may be utilized to adjust and/or control the operation of the thermal processing station 12.

Figure 2:
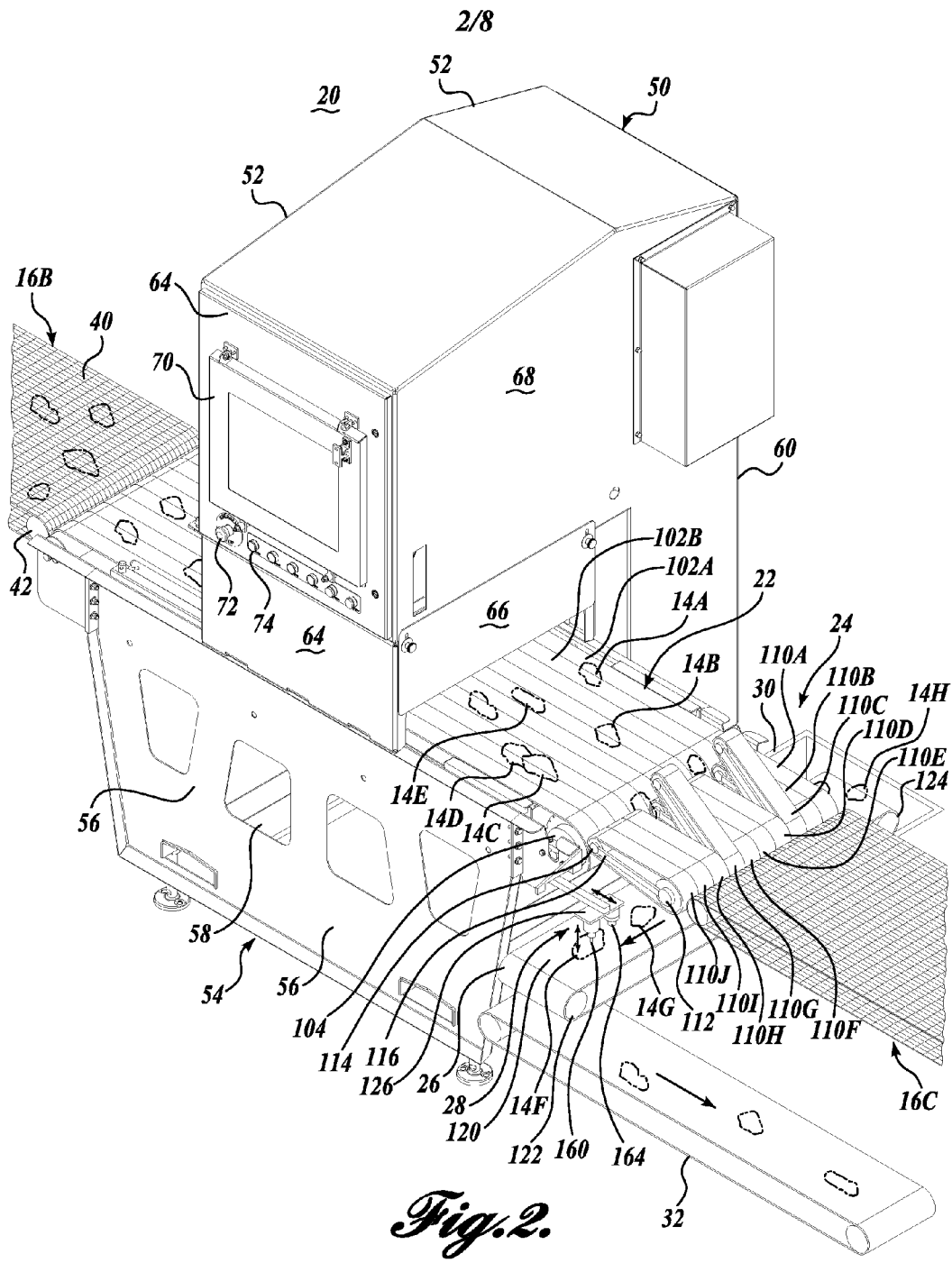
FIG. 2 is a pictorial view of a subsection of the thermal process control system of the present disclosure, with some components shown schematically.
Figure 3:
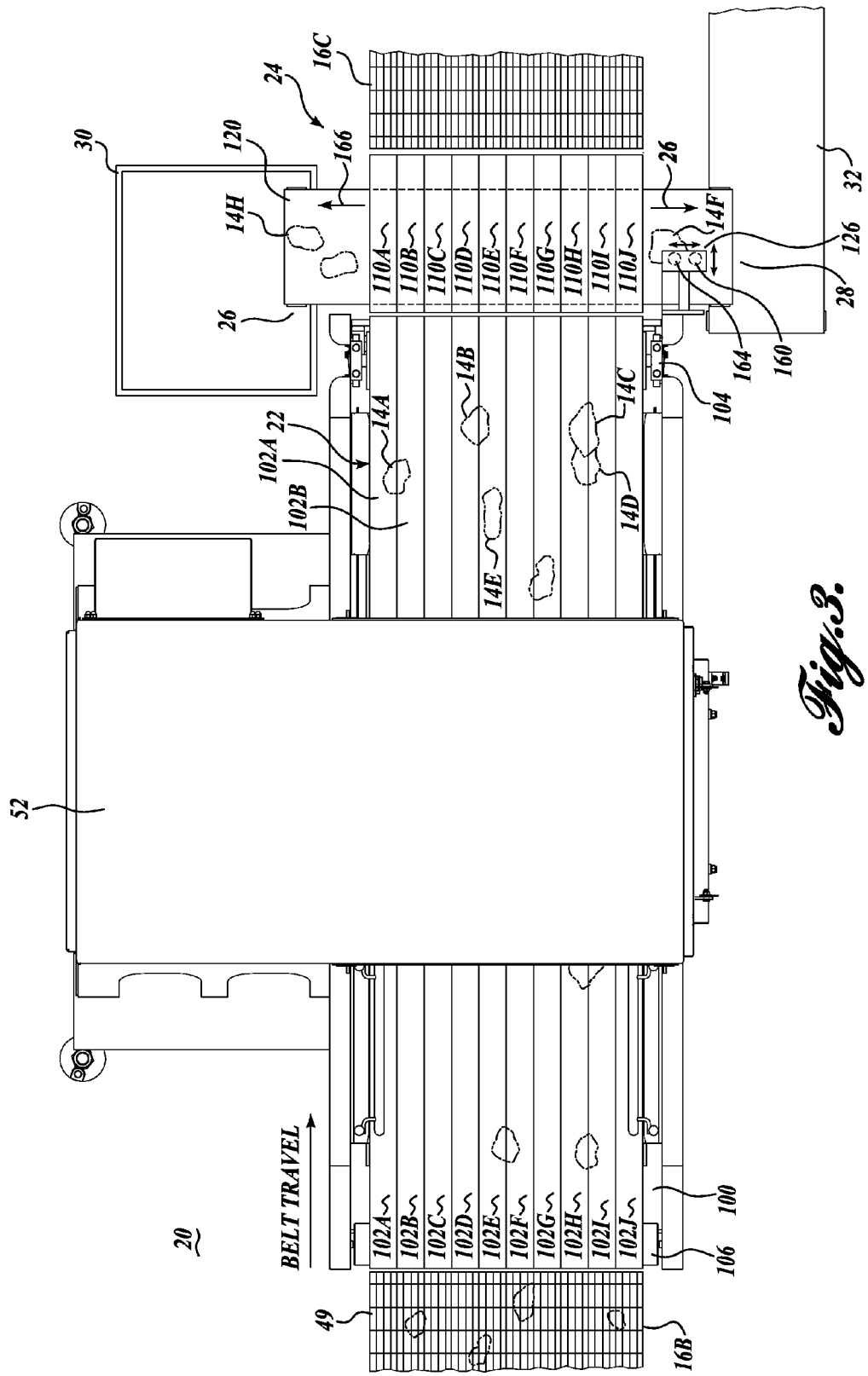
FIG. 3 is the top plan view of FIG. 2.

Describing the above basic components of system 10 in greater detail, the conveyor 16 may be of various standard constructions and powered in a standard manner. The conveyor 16 is illustrated in FIGS. 2 and 3 as utilizing an open mesh or link-type belt 40 that is trained around roller assemblies, including roller assembly 42, that may be powered or unpowered. An encoder, not shown, may be integrated into conveyor system 16, including sections 16A and 16B. The encoder may be configured to generate pulses at fixed distance intervals corresponding to the movement of the conveyor thereby to indicate the speed and displacement of the conveyor, which information can be used to keep track of the locations of food products 14 carried by the conveyor once identified at scanning stations 18 and/or 20.

Scanning stations 18 and 20 may have constructional and operational features that are very similar or the same and thus, the following description, unless otherwise indicated, applies to both scanning stations 18 and 20, though only scanning station 20 will be specifically referenced in detail. The scanning station 20 includes a scanning device 50 having a housing 52 positioned above conveyor section 22 and supported by an underlying frame 54. As shown in FIG. 2, the frame includes major side panels 56, extending lengthwise of conveyor section 22, and are transversely connected together by a plurality of cross-members 58. The cross-members 58 also tie into a housing base portion 60 that extends downwardly from housing upper portion 52 to the level of the floor 62 on which the scanning station 20 rests.

The housing upper section 52 includes a forward face panel 64 that extends downwardly to be supported by frame 54, see FIG. 2. Removable side skirt panels 66 depend downwardly from the side panels 68 of the upper housing section 52 to fairly closely overlie conveyor section 22. The side skirt panels 66 are used to contain the light utilized in conjunction with the operation of the scanning station 20. However, such panels are removable when requiring access to conveyor section 22, for instance, for cleaning or servicing.

A touch screen interface panel 70 is shown as mounted on housing forward face 64. Also various control knobs 72 and 74 are positioned beneath the touch screen panel 70 for use in operating the scanning station 20 and optionally for other purposes.

The scanning stations 18 and 20 may utilize a variety of different scanning technologies in the visible light as well as hyperspectral range. One visible light technology employs a video camera (not shown) to view workpieces, such as food products 14, along a line of sight which is schematically labeled as 80, see FIG. 4. The workpieces 14 are illuminated by one or more light sources, for example, by a laser beam, schematically depicted as part number 82 in FIG. 4. The laser beam 82 extends across the moving conveyor section 22 to define a sharp shadow or light stripe line, with the area forwardly of the transverse laser beam being dark. When no workpiece is being carried by the conveyor section 22, the shadow line/light stripe forms a straight line across the conveyor section. However, when a workpiece 14 passes across the shadow line/light stripe, the upper, irregular surface of the workpiece produces an irregular shadow line/light stripe as viewed by the camera, which is directed diagonally downwardly on the workpiece and the shadow line/light stripe. The camera depicts the displacement of the shadow line/light stripe from the position it would occupy if no workpiece were present on conveyor belt section 22. This displacement represents the thickness of the workpiece along the shadow line/light stripe. The length of the workpiece is determined by the distance of the belt travel of conveyor 22 that shadow lines/light stripes are created by the workpiece. In this regard, an encoder, not shown, is utilized in conjunction with conveyor 22, with the encoder generating pulses at fixed distance intervals corresponding to the forward movement of the conveyor 22.

In lieu of a video camera and light source, the scanning stations 18 and 20 may instead utilize an X-ray apparatus (not shown) for determining the physical characteristics of the workpieces 14, including their shape, mass, and weight. X-rays may be passed through the workpiece in the direction of an X-ray detector (not shown) located beneath conveyor 22. Such X-rays are attenuated by the workpieces 14 in proportion to the mass thereof. The X-ray detector is capable of measuring the intensity of the X-rays received thereby, after passing through the workpieces. This information is utilized to determine the overall shape and size of the workpieces, as well as a mass thereof. An example of such X-ray scanning device is disclosed in U.S. Pat. No. 5,585,603, incorporated by reference herein. The foregoing scanning systems are known in the art, and thus are not novel per se. However, the use of these scanning systems in conjunction with other aspects of the described embodiments are believed to be new.

Scanning in the hyperspectral range can be by reflectance spectroscopy techniques or by the use of other existing technology.

The data and information measured/gathered by the scanning stations 18 and 20 are transmitted to computing device 34, which is capable of recording the location of the work products 14 on the conveyor section 22 as well as the shape, thickness, size, outer perimeter, area, exterior condition or texture, and other physical parameters of the work products. The computing device 34 can be used to determine and record these physical parameters with respect to the work products as they exist on the conveyor section 22. As discussed below, the computing device 34 can also be used to record the temperature of the work products as measured downstream from scanning station 20 at temperature measuring station 28. In addition, the computing device, upon the information received from scanning system 18, can initiate various actions including, for example, altering the process conditions for the thermal processing station 12, notifying personnel of problems in the manner in which work products are being processed at station 12, or diverting work products from the processing station 12, for example, the work products that are outside of an acceptable range of one or more physical parameters, such as maximum thickness.

The computing device also can be used to record physical parameters of the work product 14 prior to processing at thermal processing station 12 and then subsequent to such processing, whether such processing involves cooking by steaming, frying, baking, roasting, grilling, boiling, etc. As discussed more fully below, optionally system 10 may utilize only one of the scanning stations 18 and 20. If only scanning station 18 is utilized, the information from scanning station 18 can be used to model the workpieces even after being thermally processed at station 12. Although typically shrinkage or change in shape of workpieces after thermal processing is not symmetrical and not easily quantifiable, such change is capable of being modeled with the use of a computing device. Such models and the data relative thereto may be stored in the memory portion 90 of the computing device. Such models and data can be employed to determine physical aspects of the workpieces after thermal processing and before measuring the temperature of the workpieces at thermal measurement station 28.

As shown in FIG. 1, the computing device 34 includes a central processing unit 92 as well as a memory 90. As noted above, the data concerning the workpieces, including their shapes, sizes, weights, and thicknesses, as well as the effect on the workpieces of further processing, may be stored in the computer memory 90. The information stored in memory can be easily selected by the user via interface 70 in the form of a touch screen panel or other interface device.

As also shown in FIG. 1, the computing device 34 may be in communication with a network system 94, which enables the computing device to communicate with and share information with other computers. The computing device 34 may also control and drive other equipment and hardware that is described below in addition to the scanning stations 18 and 20, the conveyor 16 and conveyor section 22.

As briefly noted above, the thermal processing station 12 may be used to process the workpieces in the form of food products in one or several manners. For example, one or more cooking processes may be utilized. For example, the food products may be cooked by steaming, frying, baking, roasting, grilling, boiling, etc. In this regard, the cooking processes may be carried out by convection, conduction, condensation, radiation, microwave heating, or by other techniques or systems. Also, different heating media may be utilized in the cooking process, including utilizing heated air or water, as well as steam.

In one typical thermal processing station configuration, the heating medium used for cooking, frying, baking, or roasting in an oven or frying in a fryer, or boiling, is supplied via a large, remotely located, natural gas-fired heat exchanger and corresponding storage tank for a thermal fluid. The heated thermal fluid is pumped through a further heat exchanger at the oven or fryer, etc., to provide heat to the oven or fryer, or boiler, etc. The thermal heating medium is then circulated back to the heat exchanger/storage tank, where the heating medium is reheated. Typically, heating devices of this nature are generally either fully off or fully on. In this regard, if workpieces, for example food products, have not entered the oven or fryer for a period of time, the demand for the heat at the oven, fryer, etc., drops and the gas-fired heat exchanger/tank shuts off. However, if relatively suddenly a large quantity of food products enter the oven or fryer, a length of time is required before it is sensed that the oven or fryer is cooling, and that the heating medium is not being heated. By the time the heating medium is sufficiently heated again, the oven or fryer may have cooled to the level that the food product passing therethrough may be under-processed. As part of the present disclosure, scanner 18, in conjunction with computing device 34, is capable of recognizing that operation of a thermal processing station may have slowed or even stopped, but suddenly needs to be restarted due to the arrival of food products to the thermal processing station. A signal is sent to the gas-fired heat exchanger/tank to immediately restart, and thereby minimize temperature swings in the food products processed at the thermal processing station. The present disclosure is capable of carrying out this "feed forward" control function. In this regard, the scanner 18 functions as a food product flow sensor.

The thermal processing via system 10 is not limited to cooking of the food products, but rather could involve the chilling, proofing, drying, or freezing of the food products. In this regard, the thermal processing station 12 may be a chiller, proofer, dryer, freezer or similar system and the thermal medium can be a chilled or low temperature fluid medium that is cooled by a refrigeration system.

As noted above, the workpieces in the form of food products 14 or other type of workpieces may be transported through the thermal processing station 12 by a conveyor system 16 or other transport system. It is common in industrial thermal processing stations for the station to have its own internal conveyor system to move the food products through the station while the food products are being thermally processed.

Various control parameters may be utilized in the operation of the thermal processing station 12. Such control parameters may include, but are not limited to, the speed at which the workpieces in the form of food products are transmitted through the station, as well as the volume or mass of the food products passing through the thermal processing station per unit of time. The control parameters may also include the humidity within the thermal processing station, as well as the temperature of the heat transfer medium, whether hot or cold air, hot or cold liquid, or other medium. If microwaves are utilized in the thermal processing station, the intensity level of the microwaves can be used as a control parameter.

As noted above, a conveyor section 22 is utilized in conjunction with scanning station 20. The conveyor section 22 includes a belt 100 that is of one piece construction or optionally can be divided into a plurality of separate lanes for example, 102A through 102J. Such lanes may be created or indicated on belt 100 by vibratory laning posts, striping, indentations or ridges formed in the belt itself, or other means. The belt 100 trains around a downstream powered roller assembly 104 and an upstream idler roller assembly 106. Although not shown, one or more tensioning rollers may be utilized, for example, in conjunction with the lower return run of belt 100. An encoder, not shown, may be utilized in conjunction with belt 100 so that the scanning station 20 is capable of keeping track of the location of the various workpieces, for example, food products 14, identified and characterized by the scanning device 50 of the scanning station. In this regard, the scanner 50 can determine the physical parameters of the food products, including their size, shape, and thickness, as well as the location of the food products on the conveyor belt 100, and in particular, what lane or lanes in which a particular food product is located. The scanner is also capable of ascertaining whether food products may be overlapping each other, such as food products 14C and 14D, shown in FIG. 2.

A diverter conveyor section 24 is located in registry with the downstream end of conveyor 22. The purpose of the diverter section 24 is to divert selected food products 14 from conveyor 22 to a underlining transverse conveyor 26, on which food products are supported during temperature measurement thereof. The diverter conveyor 24 includes individual conveyor lanes 110A through 110J. Each of the conveyor lanes trains around a drive roller assembly 112 and an idler roller assembly 114 that are connected to opposite ends of a frame 116 extending between the drive roller assembly and idler roller assembly.

As shown in FIGS. 2 and 3, each of the conveyor lanes 110A through 110J are aligned with corresponding conveyor lanes 102A-102J of belt 100 of conveyor 22 associated with scanning station 20. In addition to being individually powered, each of the diverted conveyor lanes 110A-110J may be selectively pivoted individually or in pairs or groups about drive roller assembly 112, thereby pivoting upwardly the opposite upstream end of the conveyor lane(s) so that the food product being carried by the corresponding lane(s) of belt 100 falls off the belt 100 and onto the transverse conveyor 26 that underlies diverter conveyor 24. For food product 14A, only conveyor lane 110B needs to be pivoted upwardly to enable the food product to drop down to transverse conveyor 26. However, for food product 14B, conveyor lanes 110D and 110E must both be pivoted upwardly to enable food product 14B to drop down onto transverse conveyor 26. Once the selected food product has dropped downwardly from belt 110 to transverse conveyor 26, the applicable conveyor lane(s) 110A-110J may be returned to its normal operational position. If the food product in question is not to be diverted onto the transverse conveyor 26, the food product simply passes over the diverter conveyor 24 and onto the conveyor section 16C of the main conveyor 16.

The transverse conveyor 26, as noted above, is located below the diverter conveyor 24. The transverse conveyor includes a belt 120 trained about end rollers 122 and 124, one or both of which may be powered to drive the belt in either direction along the length of the conveyor, thereby to position the selected food pieces 14 at a temperature measuring station 28 adjacent one side of diverter conveyor 24, or a receptacle 30 located beneath the opposite end of the belt 120. One purpose of the transverse conveyor 26 is to position work products, such as food product 14F, in a proper location so that the temperature of the food product may be measured at the temperature measurement station 28.

The temperature measurement station 28 includes an extendible temperature probe 160 mounted on a single or multiple axis carriage system 126 located slightly laterally from the transfer conveyor 26. Carriage system 126 can be of various configurations, including an X-Y powered slide system. Rather than the carriage system, the thermal probes 160 may be mounted on a rotating arm structure wherein the probe is movable lengthwise of the arm, and the arm is rotatable about a vertical axis. A scanning device in the form of a camera 164 may be utilized in conjunction with a temperature probe 160 to help position the temperature probe relative to the food product in question. In this regard, the camera can be used to locate the centroid of the food product or the center of mass of the food product. The temperature probe 160 can be of various types of configurations. In one form, the temperature probe 160 can be of a thermocouple construction. The data from the temperature probe 160 can be transmitted to computing device 34, either by hardwire or by wireless transmission. This information can be processed to determine whether or not the food product has been sufficiently thermally treated, for example, if heated to a sufficiently high temperature to be cooked to a desired level, or cooled to a sufficiently low temperature. If the temperature processing of the food product has not been sufficient, the transverse conveyor can be powered in the direction of arrow 166 to deposit the food product into container 30 for re-processing. Rather than utilizing the container 30, a takeaway conveyor, not shown, can be substituted to transfer the identified food product for further processing or re-processing.

If, on the other hand, the food product has been adequately/properly thermally processed, the transverse conveyor 26 can be operated to deposit or transfer the food product in question to return conveyor 32, which then places the food product back into the main stream of processed food products moving along conveyor 16.

As noted above, temperature probe 160 is designed to extend downwardly into the food product to measure the temperature thereof. In this regard, the temperature probe may be mounted on a linear actuating device, which could take many forms, including, for example, a pneumatic or hydraulic cylinder, a roller screw actuated by a rotating nut, a piezoelectric actuator, etc. Such actuators are articles of commerce. Although a singular thermal probe 160 is shown in FIGS. 2-5, instead two or more probes may be used, thereby to measure the temperature at different locations in the food product. This can provide a more accurate measurement of the actual temperature of the food product.

Figure 4:
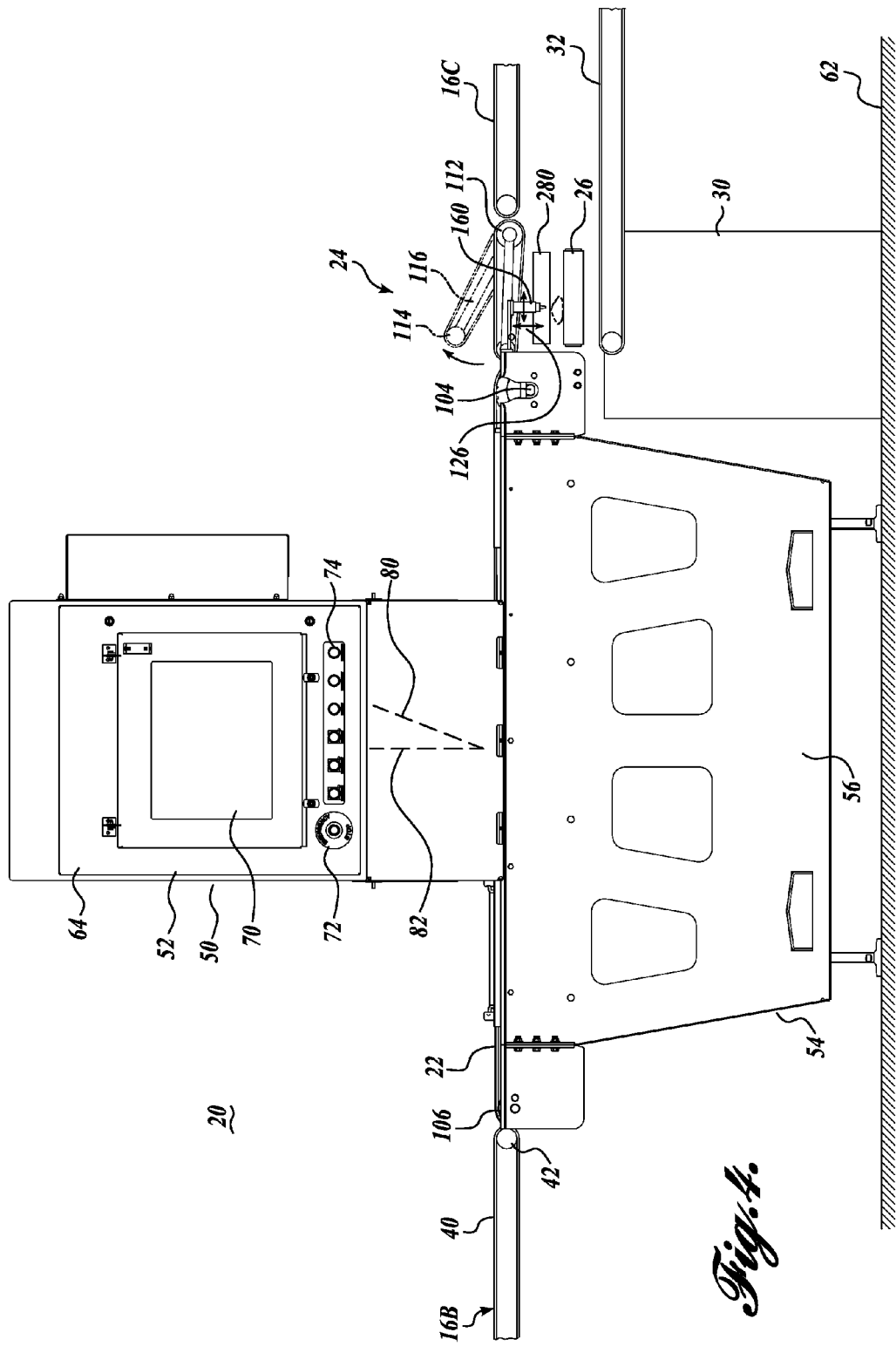
FIG. 4 is a side elevational view of FIG. 2.
Figure 5:
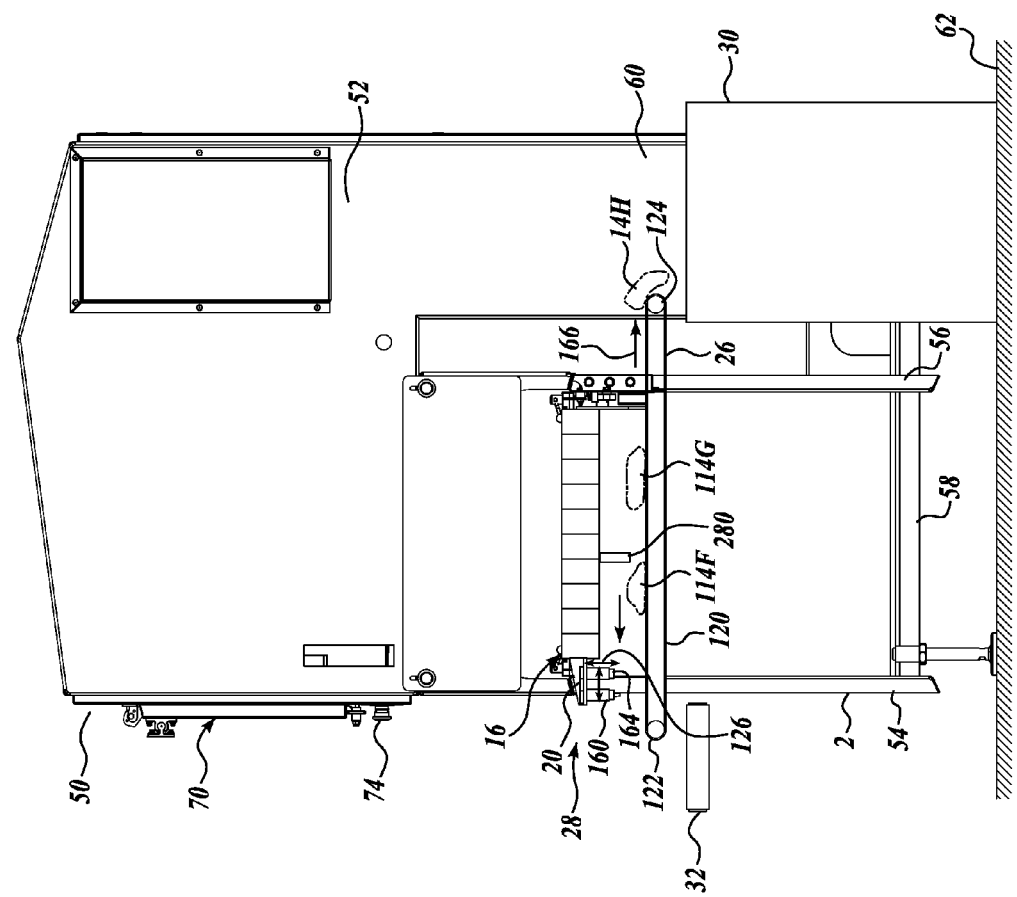
FIG. 5 is a front elevational view of FIG. 2.

As noted above, and as shown in FIGS. 2 and 3, it may be that workpieces, such as food products 14D and 14E, are at least partially overlapping each other on the scanning conveyor 22, or when dropped off the scanning conveyor, and then landing on the transverse conveyor 26. If the food products are in an overlapping condition on the transverse conveyor, there is a reduced likelihood of obtaining an accurate temperature measurement of the food product. To reduce this possibility, one or more abutment walls 280 extend transversely above and across transverse conveyor 26, as shown in FIG. 4. The lower edge of the abutment wall 280 is spaced above the upper surface of transverse conveyor belt 120 at an elevation higher than the thickness of a single food product, but not as high as the elevation of a second food product, if stacked on a lower food product. As a consequence, via the operation of the transverse conveyor 26, the abutment wall 280 will bear against the upper food product and separate the upper food product from the lower food product. It will be appreciated that one or more abutment walls of the nature of abutment wall 280 may be utilized along the length of the transverse conveyor 26.

Figure 6:
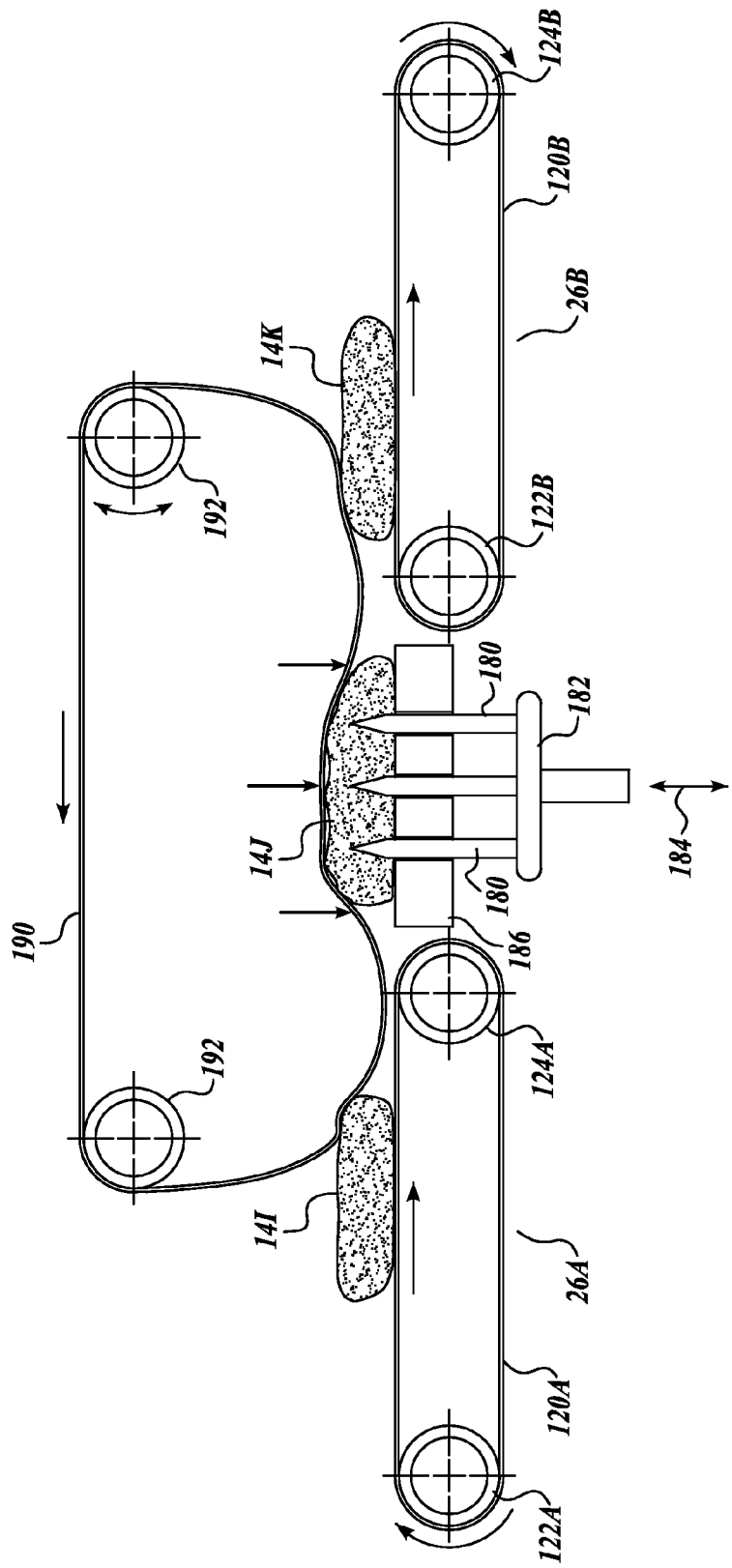
FIG. 6 is an enlarged, fragmentary view of another aspect of the present disclosure.

FIGS. 2-5 illustrate the thermal probe 160 extending downwardly into the workpiece in the form of food product 14, FIG. 6 shows a further embodiment for measuring the temperature of the food product, wherein three temperature probes 180 are illustrated as mounted on the base 182 for vertical movement in the direction of arrow 184. Temperature probes 180 extend through close fitting through holes formed in platform 186 on which food product 14J is positioned. The food product 14J is moved toward the platform 186 by transverse conveyor section 26A. Such conveyor section includes an endless belt 120A trained around end roller assemblies 122A and 124A. The transverse conveyor section 26A advances the food product 14 towards the platform 186, and when the food product approaches the platform, an overhead belt 190 that is draped over and overlies a portion of belt 120A engages the top surface of the food product 14 to urge the food product from the belt 120A and onto temperature measuring platform 186. One or more sensors determines that the food product has reached the proper measurement location, halts the conveyors 26A and 190 and initiates the upward movement of the probes 180. The overhead belt 190 is trained about upper roller assemblies 192, one or more of which can be powered to rotate in the desired direction. The belt is draped over the food product 14J and conforms to the contour of the top surface of the food product, but is capable of urging/moving the food product from belt 120A onto the platform 186. This enables the food product 14J to be placed in desired position while retaining the shape of the food product. Further details on this type of conveyance system are set forth in U.S. patent application Ser. No. 12/186,445, which is incorporated by reference into the present application.

While the food product is positioned on the platform 186, the overhead belt 190 is stationary and can apply a downward load on the food product to hold the food product in place while the temperature probes 180 are inserted upwardly into the food product. Once the temperature of the food product has been measured, the probes 180 are retracted downwardly so that they are withdrawn from the food product, thereby allowing the belt 190 to move the food product onto transverse belt section 120B for movement away from the temperature measuring platform 186. The belt section 26B, like belt section 26A, includes an endless belt 120B that is trained about end roller assemblies 122B and 124B. The transverse belt section 26B can direct the food product 14 to various locations including, for example, to a location for re-processing if need be, or to rejoin the other food products for further processing in the normal course.

As noted above, probes 180 are carried by a base 182 for vertical movement in the direction of arrow 184. The movement of the probes 180 is preferably in a prescribed manner, wherein the probes 180 are initially inserted quite quickly to a sensing position that is somewhat below the middle of the thickness of the food product 14J. Thereafter, the probes are moved upwardly more slowly to approximately the center of the thickness of the food product and then somewhat beyond the center of thickness of the food product. Thereafter, the probes are relatively quickly withdrawn downwardly. This prescribed motion of the probes 180, is based on the premise that the exact center of the thickness of the food product may not be accurately known, and there may be voids in the food product that can result in an erroneous reading. However, by taking many readings during the slower motion of the probes through the middle of the food product, the lowest temperature of the food product can be determined. This lowest temperature can then be analyzed regarding whether a thermal processing of the food product has properly occurred. Of course, if the food product is to be cooled or frozen, then through the prescribed motion of the temperature probes 180, the highest temperature of the food product can be found by the foregoing technique.

Periodically, the temperature probes 160 and 180 are cleaned or otherwise treated so that they remain in sanitary condition. This can be accomplished by numerous techniques, such as by induction or convection heating, heating by steam or hot air, heating by electromagnetic radiation, or heating by electrical current. The temperature probes may be sterilized after each use, or after a selected number of uses.

Figure 7:
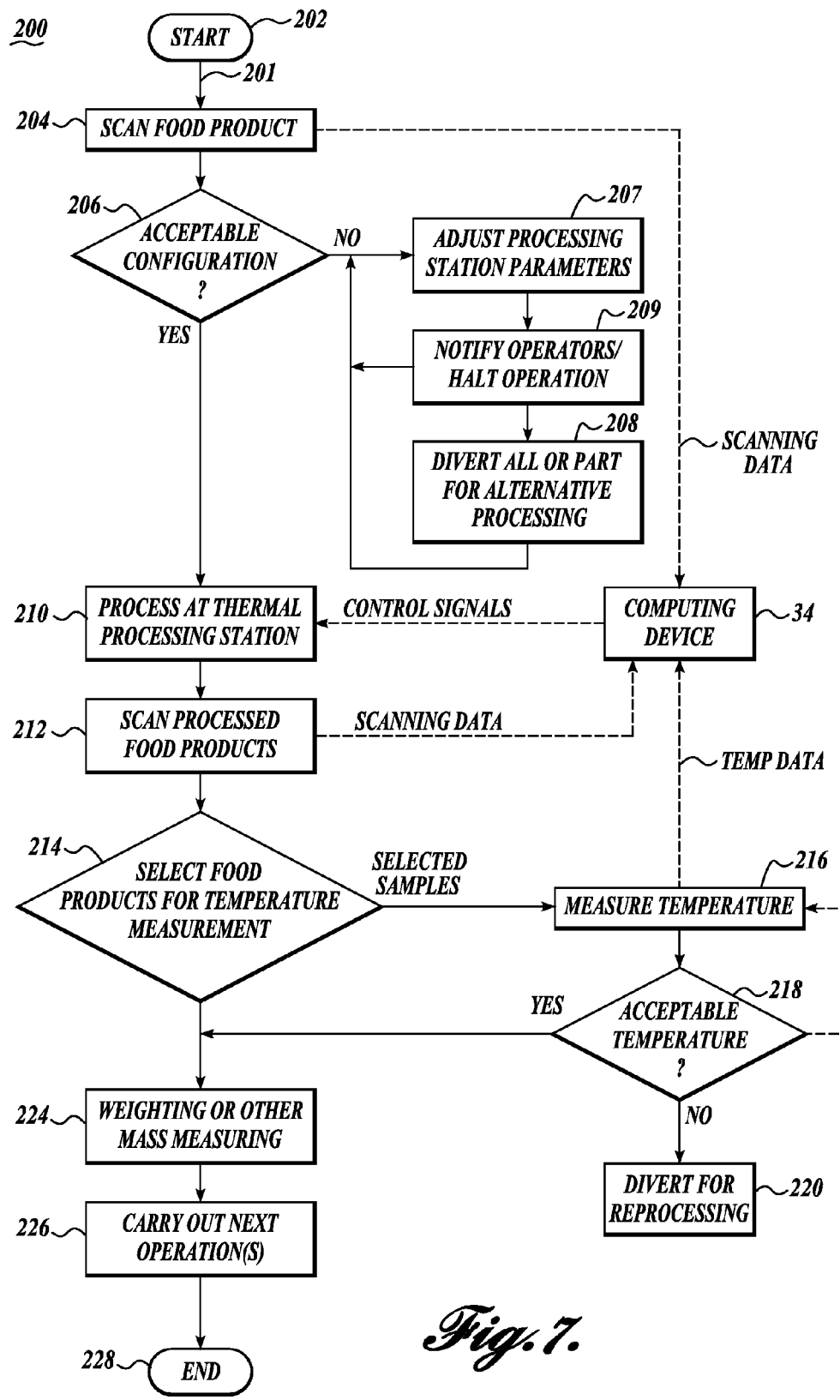
FIG. 7 is a flow diagram of one method of the present disclosure.

An overall method 200, in accordance with the present disclosure, is illustrated in the flow chart of FIG. 7. The method starts at 202 and includes step 204 of scanning workpieces, for example, food products traveling along a product stream 201 toward a thermal processing station, such as station 12 shown in FIG. 1. The food products are scanned, and the scanning data is used to determine physical attributes of the food products, including, for example, the volume, mass, thickness, centroid, area, texture, surface condition, and other physical features of the food products. In this regard, the scanning data is transmitted to computing device 34 for processing and analysis of the scanning data. Based on the data received from the scanning step 204 and the analysis of that data by computing device 34, various actions can be taken at step 206 that are initiated by output signals from the computing device 34. As a first possibility, at step 207 the computing device may send operational signals to the thermal processing station to alter process parameters at the thermal processing station, for example, as noted above, the humidity in the thermal processing station and/or temperature of the heating/cooling medium used for thermal processing. Also, the processing time of the food product in the thermal processing station may also be altered. Signals may be also sent to other components of the control system 10 which have an effect on the processing of the food products, for example, the speed at which food products enter the thermal processing station.

In addition, as described above, the information from the scanning step 204 can be used as a feed forward control system to control the operation of the heating or cooling system used for thermal processing at processing station 12.

As an alternative to directly varying the process parameters of the thermal processing station or operational parameters at other locations of the process control system 10, the determination at step 206 may instead cause the computing device 34 at step 209 to send a notification to operational personnel that adjustments are required in the processing of the food products or that significant problems exist at the thermal processing station or elsewhere. Notification of operational personnel can be via different means, including email, telephone call or message, pager, horn, or other audio signal, flashing lights, etc. In addition to or as an alternative to sending notifications to operational personnel, the control system of the present disclosure could stop the processing of the food product, including shutting down the thermal processing station. Control specifications or limits can be set in advance so that a desired action(s) is/are taken depending on the extent of the deviation between the measured parameters or specifications from the scanning of the food products and the desired range or limits in parameters and specifications of the food products.

As a further option or possibility at step 206, a decision can be made whether food products should continue along the product stream to processing station 12 or be diverted for alternative processing at step 208. This decision is made based on the scanning data and the analysis thereof. It may be that the scanning results indicate that specific food products are either too large or too small, or too thick or too thin, etc., to be successfully processed at the thermal processing station 12. In that case, such food products that are not of acceptable configuration can be diverted to alternative processing at step 208. This diversion option is typically feasible when a majority of the workpieces are within a desired specification but there are occasional outliers, or perhaps if occasionally one food product is lying on top of another food product. By diverting the outliers, the remainder of the food products can continue on to be processed at station 12.

As a further possibility, rather than halting operation of the thermal processing system, it is possible to decide at step 206 to divert (at least for a limited time period) all of the out of parameter food products from the main flow stream 201 for alternative processing. Such diversion of the food products would require a diverting system which may be similar to diverter conveyor section 24 discussed above.

On the other hand, if the food products are of acceptable physical specification, the food products continue along the food product stream 201 to the thermal processing station 12 for the processing of the food product at step 210. Various control parameter algorithms can be utilized in conjunction with the processing that occurs at thermal processing step 210. Data for use by the control system algorithms is received from the computing device 34, which data can originate from the scanning data obtained from the scanning step 204. This process of transmitting control system information to the thermal processing station creates a closed loop system, whereby information about the food products traveling towards the thermal processing station can be factored in to the manner in which the thermal processing station is operated, including adjusting the thermal processing time of the food products and other process settings, such as the humidity within the processing station and the temperature within the processing station and/or the temperature of the heat transfer medium used to cook, cool, freeze, or otherwise process the food products at the thermal processing station.

As noted above, one of the physical parameters of the workpieces that may be modeled from the scanning data is the thickness of the food products. It is known that industrial cooking processes are very sensitive to minor differences in product thicknesses. For example, a product that is 20 mm thick can take up to 23% more time to cook than a product that is 18 mm thick under the same cooking conditions. Thus, the thickness differential of 11% between food products can result in a cook time differential of 23%. Thus, for an industrial cooking process to run efficiently, the food pieces must be near the same thicknesses. If not, and if cooking occurs based on the thickest food product, then thinner food products will typically be overcooked. Correspondingly, if the cooking process does not take into consideration the thickest food products, then the thickest food products may not be properly or sufficiently cooked.

Also, the scanning process will be able to ascertain whether food pieces are arranged fully or partially on top of each other, which can cause a risk of undercooked food pieces. These overlapping food pieces may either be rearranged or may be diverted for reprocessing at step 208.

After being processed at thermal processing station 12, the food products may be scanned by scanner 20 at scanning step 212. The scanning data from the scanning step can be transmitted to the computing device 34, as shown in FIG. 7. By scanning all of the food products leaving the thermal processing stations, particular food products can be selected for temperature measurement based on desired criteria. Such criteria may include one or more of the following physical attributes of the thermally processed food products: thickness; width; length; aspect ratio; area; volume; weight; surface temperature; color; surface texture. The thermally processed food products are selected at step 214 for either temperature measurement or for continuing along the product stream. The selection of the food products for temperature measurement can be based on various criteria, such as one or more physical attributes of the food product, by sweeping across the food product stream, and selecting food products from such sweeping procedure, from random selection, or other criteria.

If the food products are selected for temperature measurement, such food products are diverted from the main product stream 201 to a temperature measurement station 28 wherein the temperature of the food products is measured at step 216. This information is transmitted to computing device 34 for analysis. This analysis may take into consideration the time span between the food products being diverted from the main product stream 201 and when the temperature measurement actually takes place. The temperature measurement data collected may indicate that a change is needed in the control system(s) for the thermal processing station. For example, if the temperatures of the sampled food products are too low, one or more adjustments may be needed to the processing parameters at the thermal processing station. For example, the speed at which the food products pass through the thermal processing station may need to be lowered, or the temperature of the heat exchange medium used in the thermal processing station 12 may need to be increased, or other control system adjustment made. On the other hand, if the temperature of the selected samples of processed food products is too high, then appropriate adjustments can be made to one or more of the process parameters via the control system algorithms utilized in conjunction with the thermal processing station.

It is current industry practice to adjust the cooking process so that the center of the thickest food pieces reach a food safe temperature. However, this approach can cause a significant amount of the food pieces to be overcooked, which not only decreases yield, but also profit, since overcooking dries out moisture, resulting in reduced product weight and quality. Applicant estimates that overcooking on a single food processing line can have an annual negative economic value of hundreds of thousands of dollars. Moreover, if undercooking of food products can be avoided, then unscheduled line stoppage for cleaning and otherwise sanitizing the food processing line can be avoided, thereby increasing the amount of time the food processing line is operational.

Step 218 depicts the decision of whether, based on the measured temperature of the sampled food product, the food product is likely to have been acceptably thermally processed. If not, the food product can be diverted at step 220 for further processing. However, if the temperature measurement indicates that the food product has been properly processed, then the food product can proceed to further processing, including by rejoining the food product stream 201.

In addition to determining whether the food products have been acceptably thermally processed in the manner of course of the operation of system 10, the present process can also be used to monitor whether changes in the food product detected at step 201 have caused a problem in the processing step of 210. For example, if the food products were detected by the scanning step 204 as being suddenly thicker or thinner, or larger or smaller, then such changes in the physical attributes of the food products may have resulted in the adjustment of processing parameters at step 207 to the processing of food products occurring at step 210. By measuring the temperature of the food product at step 216, it is possible to determine whether or not the adjustments made at step 207 were successful or not. This can be determined by measuring the temperature of the food product after one residence time within the food processing station.

The foregoing adjustment to the processing parameters at step 207 may have been for reasons other than detecting a change in the population of the work pieces, but rather, due to other changes in the thermal processing system, for example, a desire to increase the throughput of the system, and thus needing to shorten the thermal processing time at step 210. In this regard, operational parameters of the thermal processing station may have been adjusted, and the results of such adjustment can be monitored by monitoring the temperature of the food products exiting the thermal processing station after one residence time in the thermal processing station.

Another aspect of using a scanner for scanning all of the food products at step 212 that leave the processing station is that based on the temperature measurement data, it is possible to identify other processed food products that likely are unacceptable, and thus such food products can be diverted from the main food product stream 201 using the diversion equipment and procedures discussed above. In a typical operational mode, the temperature of about one food product per minute is measured. If such measured sample food product is found to be unacceptable, such food product can be diverted for further processing. Unless all of the food products from the thermal processing station are scanned, other similar unacceptable food products will continue along the food product stream 201. However, if all of the food products are scanned, food products having attributes similar to the unacceptable food product can also be automatically diverted from the main product stream.

Another benefit of scanning all of the food products leaving the thermal processing station 12 is that it is possible to perform a thermal processing station diagnosis and performance validation. In the thermal process diagnosis mode, food products of substantially equal thicknesses, across the width of the product stream, can be selected for temperature measurement. This enables a determination to be made if the thermal processing unit is processing uniformly across the full width of the product stream. For example, if a 40 inch wide oven includes a conveyor for carrying the food products through the oven having ten lanes each four inches in width, it is possible to select, for example, only 18 mm thick food pieces that appear in each lane as they occur. The temperature of such selected food products can be measured and color or other attributes of the food products can also be determined by the scanning step 212. If the heat is too cool at the sides or edges, or if air entrainment in the equipment is affecting color development in one region or side of the food product stream, these problems can be identified as well as in which of the product lane(s) the problems are occurring. Corrective measures can be taken to rectify the situation.

In process 200, the weight or mass of the processed food products is optionally weighed at step 224. Such weighing can occur by various means, such as by use of a platform scale, a tote scale, or other mass measurement system. This information can be combined with the total food product input rate at the beginning of the process 200 to determine the yield of the process on an hourly basis, a batch basis, a shift basis, etc. This information can be utilized to adjust the process 200, including adjusting the process parameters at the thermal processing station 12. Also, this information may indicate that the assumed density of the food product being utilized in the scanning step 204 may have to be adjusted if the data from the weighing step 224 shows a deviation from the expected weight of the food products based on the starting weight of the food products and the level of diversion of the food products occurring during process 200. After the weighing step 220, the food products continue on to subsequent operations at step 226, thereby reaching the end of the process 228.

FIG. 8 illustrates a further process of the present disclosure, wherein the process 250 may be employed as a "stand alone" process to be used in conjunction with existing food processing lines or equipment. Process 250 begins at the start step 252, wherein a stream 253 of food products are transmitted to a processing station and processed at step 254. After processing, the food products are randomly or otherwise selected for temperature measurement at step 256. Such selected food products are then scanned at step 258 to model desired physical attributes of the selected food products. Modeling also enables the location of the center of mass or centroid of the food product to be located so that in the temperature measurement step 260, a temperature probe or other device may be accurately positioned at the food product centroid or geometric center. At step 262, if the temperature measurement determines that the food product sample has been satisfactorily processed, then the food product in question may be returned to the main food product stream 253, and then the process concluded at step 264. However, if the temperature of measurement indicates that the food product in question has not been properly processed, then such food product can be diverted at step 266 for further processing. The data from the scanning step 258 and/or from the temperature measurement step 262 can be transmitted to a computing device for storage and also for use in analyzing the thermal process being carried out, as well as the operation 254 of the thermal processing station.

Further, if the temperature measurement step at 260 indicates that the food product has been underprocessed, then the temperature measuring instrument may need to be sanitized, so as not to cross-contaminate subsequent food products of which the temperature is measured. Even if the temperature measurements indicate that the food products have been properly and sufficiently processed, good practice indicates that the instrumentation used to physically determine the temperature of the food products, especially if a probe or other device is inserted into the food product, sanitation thereof should occur on a periodic basis. As noted above, this can take place by various means, such as by subjecting the temperature probe or other equipment to steam, placing the temperature probe or other equipment in boiling water, or in a stream of very hot air, etc.

In process 250, first and second scanning stations 18 and 20 are not utilized. Rather, limited scanning of selected food product samples occurs primarily to model the selected food product so that the temperature probe or other temperature measuring device can be properly located with respect to the selected food product. Such scanning can occur via one or more camera devices, such as camera 164, described above. Or other well-known scanning systems can be utilized instead. Due to the limited purpose and function of such scanning, the scanning device can operate quite quickly so as to not be a significant limitation in the temperature measuring process.

Use of camera 164 or other similar scanner can result in a much more accurate temperature measurement of the food product than if operating personnel must visually select what location in a food product in which to insert a temperature probe or other measurement device, and then actually inserting the probe or device in the food product. As noted above, there are at least two sources of error in such manual operation. A first source of error occurs when determining where the optimum location exists in which to take the temperature measurement. A second source of error occurs in the actual placement of the thermal probe or other device into the food product. Nonetheless, it is contemplated that the system and methods of the present disclosure can be utilized in conjunction with manual temperature measurement of the food product. Even manual temperature measurement will provide advantages over existing techniques and methods for measuring the temperature of thermally processed food products.

It will be appreciated that through the present disclosure, it is possible to model the overall system 10 to evaluate multiple alternative values of control parameters if the results of the model indicate an issue is occurring in the thermal processing of food products or other types of workpieces. The modeling of the system can consider at least the following dynamics: (1) how changes in the flow rate of the stream of food products entering the processing station causes changes to the temperature in the processing station and/or the temperature of the heat transfer fluid (whether air, steam, or oil) used in the processing station; (2) how changes in the volume, thickness, or other geometric or physical parameters of the food product stream, particularly of the largest pieces of food products, cause changes in the heating rate of the individual food pieces in the thermal processing station; (3) how changes in the temperature of the stream of food products is related to other changes in the system or changes in the incoming food products, such as the speed of the transfer conveyor or the mass of the food products entering the processing station over time, and then updating the model of the overall system based on such measured results. As noted above, if the results of the system model indicate that the future temperature of the food products exiting the thermal processing station will be too high or too low, adjustments can be made to the processing parameters of the thermal processing station.

While illustrative embodiments have been illustrated and described, it will be appreciated that various changes can be made therein without departing from the spirit and scope of the invention.

As one change to the present disclosure, the thermal processing control system 10 may be configured with second scanning station 20, but not first scanning station 18. In this situation, changes, adjustments or corrections to the processing parameters used at the processing station will rely upon the information and data from the scanning station 20 as well as from the temperature measuring station 28. Such data can be employed by the control system algorithms used in controlling the operation of the thermal processing station. In other respects, in this modified configuration, the advantages are provided as are achieved via the thermal processing control system 10 and the thermal processing method 200, described above.

As an alternative configuration, the thermal processing control system 10 may be configured with first scanning station 18, but not with the second scanning station 20. In this situation, all of the food products entering the thermal processing station are scanned, and the scanning data is transmitted to computing device 34 for processing and analysis of the scanning data. As also noted above, by scanning all such food products, it is possible to divert from the main food product flow stream those specific food products that are not likely to be successfully processed at the thermal processing station, for various reasons; for instance, if the food products are too small or too large, or too thick or too thin.

In addition, it is possible for the food products that are scanned at scanner 18, and then thermally processed, to be modeled as to the physical attributes of the food product after being thermally processed, whether the thermal process involves cooking, and whether such cooking is by steaming, frying, baking, roasting, grilling, boiling, etc. Typically, the shrinkage that occurs from thermal processing of food products is non-symmetrical and not easily quantifiable, but is capable of being modeled, especially with the use of a computing device. Such model(s) and data relative thereto may be stored in the memory portion 90 of computing device 34. Such model(s) and data can be employed to determine physical attributes of the food products after thermal processing. This enables the ability to select specific food products for temperature measurement after being thermally processed. Use of scanning information from scanner 18 in this manner may not be as accurate as employing a second scanner 20, but may be an acceptable alternative to requiring a second scanner 20, thereby to provide the benefits of the present disclosure without requiring the second scanner 20.

As another possible change to the present disclosure, a particular configuration of an apparatus for diverting food products from the food product stream was described above through the use of a conveyor diverter section 24. However, other means and systems can be utilized for diverting food products from the main food product stream, either for temperature measurement or for alternative processing, or for other purposes. Such diversion can occur by use of gravity, openings between conveyors, or using compressed air jets to blow desired food products off of the conveyor along which the food products are being carried.

The foregoing disclosure has described the use of the transverse conveyor 26 for directing workpieces, such as food products, to a thermal processing station. Of course, other configurations of conveyors can be utilized. For example, such conveyor could be located above, below, or parallel to conveyor system 16.

Although the foregoing disclosure describes the use of diverter conveyor section 24 and transverse conveyor 26 for transporting selected workpieces, including food products, to a temperature measuring station, this function can be carried out using a robot system, which can be in the form of an X-Y actuating system that is capable of dropping down to conveyor 16 and picking up the workpiece, then carrying the workpiece to another location or another conveyor. One such system is disclosed by U.S. Pat. No. 6,826,989, which is incorporated by reference into the present application. Also, U.S. Pat. No. 7,007,807 discloses the sorting of work pieces utilizing the "pick and place" system and structure of U.S. Pat. No. 6,826,989. U.S. Pat. No. 7,007,807 is also incorporated by reference into this present application.

The embodiments of the invention in which an exclusive property or privilege is claimed are defined as follows:

1. A method for measuring the internal temperature of discrete, thermally treated workpieces, comprising:
   (a) selecting workpieces for temperature measurement from an output stream of workpieces exiting from a thermal processing system;
   (b) removing selected workpieces from the output stream;
   (c) after removal of selected workpieces from the output stream, dimensionally characterizing the removed selected workpieces; and
   (d) after dimensionally characterizing the removed selected workpieces, measuring the temperature of the selected workpieces at one or more locations expected to give a representative temperature of the workpieces based on the results of the dimensionally characterizing the selected workpieces.

2. The method according to claim 1, wherein the selected workpieces are removed to a temperature measurement station at which the temperatures of the workpieces are measured.

3. The method according to claim 2, wherein the temperatures of the selected workpieces are measured using one or more probes automatically inserted into the selected workpieces.

4. The method according to claim 1, wherein:
   the thermally treated workpieces are carried away from the thermal processing system via a conveyor system; and
   the selected workpieces are removed from the conveyor system and transported to a temperature measurement station by a transport method selected from the group consisting of:
   (i) one or more conveyors; (ii) gravity; (iii) a gap or opening in the conveyor system; (iv) pressurized air jets; (v) multidirectional pick-and-place actuator; and (vi) robotic arm.

5. The method according to claim 1, wherein the step of selecting workpieces from the output stream exiting from the thermal processing system is selected from the group consisting of:
   (a) random selection;
   (b) sweeping across the stream of workpieces outputted from the thermal processing system;
   (c) selecting the workpieces based on size; and
   (d) selecting the workpieces based on one or more physical attributes.

6. The method according to claim 1, further comprising scanning the workpieces removed from the output stream and modeling one or more physical attributes of the workpieces from the results of scanning the workpieces to dimensionally characterize workpieces.

7. The method according to claim 1, wherein determining the degree of thermal treatment occurring of the workpiece comprises ascertaining if the workpiece has reached a suitable level of thermo-treatment.

8. The method according to claim 7, further comprising analyzing the temperature measurements versus the time span between the exiting of the workpieces from the thermal processing system and the measured temperature of the workpieces to determine the degree of thermo-treatment occurring of the workpiece.

9. A method for controlling a thermal processing system for food products in a thermal processing station, comprising:

(a) monitoring a stream of food products approaching a thermal processing station to determine the physical attributes and/or condition, as well as the total mass flow rate of the food products approaching the thermal processing station, and making this data available for use by a control subsystem of the thermal processing system;

(b) monitoring process parameters of the thermal processing system;

(c) measuring the temperatures of the food products exiting the thermal processing station, and making such temperature information available for use by the control subsystem; and (d) modeling the thermal processing system by considering one or more of the following dynamics:

(i) the manner in which changes in the mass flow rate of the food products entering the thermal processing station results in changes to the temperature of the heat transfer fluid utilized to thermally process the food products;

(ii) the manner in which changes in the geometry of the food products entering the thermal processing station causes changes to the rate of temperature change in the food products in the thermal processing station; and (iii) changes in the temperature of the food products exiting the thermal processing station relative to changes in the operating conditions of the thermal processing system or changes in the mass flow rate or the physical attributes of the food products entering the thermal processing station; and (e) if the modeling results indicate that the future temperature of the food products exiting the thermal processing station is beyond a desired temperature range, the control subsystem adjusting the thermal processing system process parameters or recommending that adjustments be made to the process parameters of the thermal processing system.

10. The method according to claim 9, wherein the process parameters of the thermal processing system that may be adjusted based on the results of the modeling include a parameter selected from the group consisting of:

(i) the time that the food product spends within the thermal processing station;

(ii) the humidity of the atmosphere within the thermal processing station;

(iii) the temperature within the thermal processing station;

(iv) the air speed within the thermal processing station;

(v) the radiation within the thermal processing station;

(vi) the activation or de-activation of a heat transfer medium to the thermal processing station; and (vii) the activation or de-activation of heating or cooling the fluid medium used to heat or cool the thermal processing station.

11. The method according to claim 9, wherein the monitoring of the food products of the food product stream entering the thermal processing station includes scanning the food products.

12. The method according to claim 11, wherein based on the results of scanning of the food products entering the thermal processing station, diverting selected food products from the thermal processing station based on selected physical attributes of the food products.

13. The method according to claim 12, wherein the food products are diverted according to a physical characteristic selected from the group consisting of size, weight, shape, thickness, color, texture, condition, or appearance.

14. The method according to claim 9, wherein the step of measuring the temperatures of the food products exiting the thermal processing station comprises selecting food products from the output of the thermal processing station for temperature measurement.

15. The method according to claim 14, wherein the step of selecting food products from the food product stream exiting the thermal processing station comprises scanning the food products exiting the thermal processing station, and selecting candidate food products for temperature measurement.

16. The method according to claim 9, further comprising measuring the temperature of selected food products exiting the thermal processing station, wherein the selection of food products includes selecting by a process chosen from the group consisting of:

(a) random selection;

(b) sweeping across the stream of food products output from the thermal processing station; and (c) selecting the work pieces based on one or more physical attributes.

17. The method according to claim 9, wherein if the monitoring of the stream of food products entering the thermal processing station has detected a changed population of the food products, or if the thermal control parameters have been adjusted based on the modeling results, then after one residence time of the food products in the thermal processing station, the temperature of the food products exiting the thermal processing station is measured to determine if the changes in the population of food products has caused a problem in the thermal processing station and/or if the adjustments made to the operation of the thermal processing system have timely resolved problems in the thermal processing of the food products.

18. The method according to claim 9, wherein the temperature of the food product exiting the thermal processing station is measured via probes automatically inserted into the food products.

19. The method according to claim 9, wherein the step of measuring the temperature of the food products exiting the thermal processing station includes diverting selected food products from the stream of food products exiting the thermal processing station and directing the diverted food products to a temperature measurement station.

20. A method for thermally processing a stream of food products at a thermal processing station under process parameters, comprising:

(a) selecting food products for temperature measurement from the food product stream;

(b) after selecting the food products for temperature measurement, physically characterizing the selected food products;

(c) after physically characterizing the selected food product for temperature measurement, measuring the temperature of the selected food products at one or more locations within the selected food products expected to give representative temperature of the food product; and (d) analyzing the temperature measurement results to determine if any changes are needed in the process parameters of the thermal processing station, and if said analysis indicates that changes are needed in the process parameters of the thermal processing station, transmitting control signals to change the applicable process parameters.

21. The method according to claim 20, wherein the thermal processing station is a station selected from the group consisting of a roaster, a fryer, a steamer, an oven, a proofer, a dryer, a chiller, and a freezer.

22. The method according to claim 20, wherein the step of selecting food products for temperature measurement includes scanning the food products and selecting specific food products for temperature measurement based on the results of the scanning.

23. The method according to claim 20, wherein the step of physically characterizing the selected food products for temperature measurement includes scanning the selected food product and physically modeling the scanned food product based on the scanning results.

24. The method according to claim 20, wherein the step of measuring the temperature of the selected food products comprises automatically inserting a thermal probe into the selected food product.

25. The method according to claim 20, wherein the step of analyzing the temperature measurements of the selected food products includes determining if the workpiece has been sufficiently processed in the thermal processing station.

26. The method according to claim 25, wherein the step of determining whether the food product has been sufficiently processed at the thermal processing station includes determining if the workpiece has reached a suitable degree of thermal treatment.

27. The method according to claim 20, wherein the selected food products are removed from the food product stream prior to measuring the temperature of the selected food product.

28. The method according to claim 20, wherein prior to the thermal processing, the food products are scanned and based on the results of such scanning, taking one or more steps selected from: removing from the food product stream the food products that will not be properly thermally processed at the thermal processing station; adjusting the process parameters of the thermal processing station; recommending that adjustments be made to the process parameters of the thermal processing station; halting operation of the thermal processing station; and diverting the stream of food products from the thermal processing station.

29. The method according to claim 20, wherein the process parameters for the thermal processing station are selected from the group consisting of: the time that the food product remains in the thermal processing station; the humidity of the atmosphere in the thermal processing station; and the temperature of the heat transfer medium used in the thermal processing station to thermally process the food products; the volume of the food product within the thermal processing station; the mass of the food product within the thermal processing station; the air velocity throughout the entirety or sections of the thermal processing station; and the operation of the heating or cooling system used to heat or cool the heat transfer medium used in the thermal processing station to thermally process the food products.

30. A method for optimizing the process parameters of a thermal processing station used to process workpieces, comprising:
(a) scanning the workpieces that exit the thermal processing station;
(b) physically modeling the scanned workpieces based on the data resulting from the scanning of the workpieces;
(c) selecting the workpieces for temperature measurement based on the modeling of the workpieces;
(d) removing the selected workpieces to a temperature measurement station;
(e) measuring the temperature of the selected workpieces at the temperature measurement station; and
(f) analyzing the temperature measurement results to determine if changes should be made to the process parameters of the thermal processing station.

31. The method according to claim 30, wherein the temperatures of the workpieces are measured after arrival at the temperature measurement station.

32. The method according to claim 30, wherein:
the thermally treated workpieces are carried away from the thermal processing system via a conveyor system; and
the selected workpieces are removed from the conveyor system and transported to a temperature measurement station by a transport method selected from the group consisting of:
(i) one or more conveyors; (ii) gravity; (iii) a gap or opening in the conveyor system; and (iv) pressurized air jets.

33. The method according to claim 30, wherein the step of selecting the workpieces from an output stream of the thermal processing system comprises selecting the workpieces based on one or more physical attributes.

34. The method according to claim 30, wherein the process parameters of the thermal processing station are selected from the group consisting of: the length of time the workpiece remains in the thermal processing station; the humidity of the atmosphere in the thermal processing station; the temperature of the heat transfer medium used in the thermal processing station to thermally process the workpieces; the mass of the workpieces within the thermal processing station; and the air velocity throughout the entirety or sections of the thermal processing station.

* * * * *